United States Patent [19]

Katz

[11] 4,276,206

[45] Jun. 30, 1981

[54] IMMUNOCHEMICAL CONJUGATES: METHOD AND COMPOSITION

[75] Inventor: David H. Katz, La Jolla, Calif.

[73] Assignee: Scripps Clinic & Research Foundation, La Jolla, Calif.

[21] Appl. No.: 120,067

[22] Filed: Feb. 11, 1980

Related U.S. Application Data

[60] Division of Ser. No. 4,333, Jan. 18, 1979, Pat. No. 4,220,565, which is a continuation-in-part of Ser. No. 764,586, Feb. 2, 1977, Pat. No. 4,191,668.

[51] Int. Cl.³ .................... C08L 77/04; C08L 89/00; A61K 37/02; A61K 37/26
[52] U.S. Cl. ............................ 260/6; 260/112 R; 424/12; 424/78; 424/85; 424/88; 424/91
[58] Field of Search ............... 260/6, 112 R; 424/12, 424/78, 88, 85, 91

[56] References Cited

U.S. PATENT DOCUMENTS 3,794,630  2/1974  Mullan et al. .................. 260/112 R
4,191,668  3/1980  Katz ................................ 260/6

OTHER PUBLICATIONS

Nossal et al. J. of Exp'l Med. vol. 138(1973), pp. 312–317.
Eshhar et al. J. Immunol. vol. 114, No. 2 (1975), pp. 872–876.
Bitter-Suermann et al.; Chem. Abstracts, vol. 83, 129,895p (1975).
Mosier et al. Chem. Abstracts, vol. 83: 191,237d (1975).
Eshhar et al. Chem. Abstracts, vol. 85: 121,584g (1976).

Primary Examiner—Howard E. Schain
Attorney, Agent, or Firm—Knobbe, Martens, Olson, Hubbard & Bear

[57] ABSTRACT

Techniques for preparing stable conjugates of protein-D-GL which can then be isolated in pure form are disclosed, using hen egg ovalbumin (OVA) as a prototype protein, and conjugation and purification methods are described which involve (1) application of a coupling method employing m-maleimidobenzoyl-N-hydroxysuccinimide ester (MBS) as the coupling reagent, and (2) introduction of biotin moieties into D-GL molecules to allow application of avidinbiotin system for affinity chromatographic purification of conjugates. These methods are applicable to the preparation of D-GL conjugates of insulin and Ragweed Antigen E and are of general applicability.

3 Claims, 9 Drawing Figures

CHEMICAL COUPLING OF PROTEIN TO
D-GL USING PROTEIN (OR D-GL) CONJUGATED WITH A
MALEIMIDE GROUP AND THIOLATED D-GL (OR PROTEIN)

MBS = m Maleimidobenzoyl-N hydroxysuccinimide ester

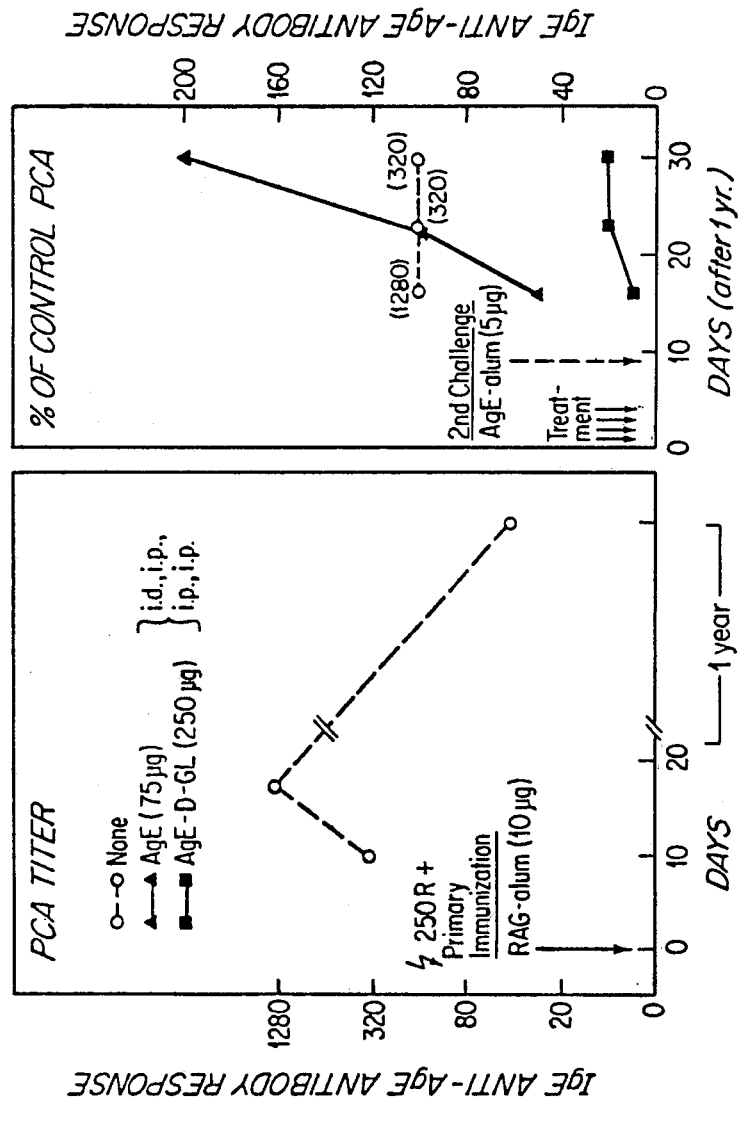

IMMUNOCHEMICAL CONJUGATES: METHOD AND COMPOSITION

CROSS-REFERENCE TO RELATED APPLICATION

This is a division of application Ser. No. 4,333, filed Jan. 18, 1979 now U.S. Pat. No. 4,220,565, which in turn, is a continuation-in-part of application Ser. No. 764,586, filed Feb. 2, 1977 now U.S. Pat. No. 4,191,668, INDUCTION OF IMMUNOLOGICAL TOLERANCE, by David H. Katz, the sole inventor of the subject matter of the present invention, now pending.

TECHNICAL FIELD

This invention relates to methods of forming antigen conjugates with D-glutamic acid-D-lysine copolymers for forming substances which are useful in inducing immunological tolerance.

The following abbreviations are used:

| | |
|---|---|
| D-GL: | a synthetic copolymer of D-glutamic acid and D-lysine, poly (D Gly$^{60}$ D Lys$^{40}$) (J. Biol. Chem. 247, 323 (1972)), and equivalent copolymers |
| OVA: | ovalbumin |
| MBS: | m-maleimidobenzoyl-N-hydroxysuccinimide |
| SHA: | s-acetylmercaptosuccinic anhydride |
| MB-OVA (or -D-GL): | m-maleimidobenzoy-OVA (-D-GL) |
| SH-D-GL (or -OVA): | mercaptosuccinyl-D-GL (-OVA) |
| MB-In (or AgE): | m-maleimidobenzoyl-Insulin (-Ragweed Antigen E) |
| SH-In (or AgE): | mercaptosuccinyl-Insulin (-Ragweed Antigen E) |
| MB-Antigen: | m-maleimidobenzoyl-antigen |
| SH-Antigen: | mercaptosuccinyl-antigen |
| PBS: | phosphate-buffered saline, 0.01 M sodium phosphate buffer, pH 7.2, 0.15 M NaCl |
| HPP: | 3-(4-hydroxyphenyl) propionyl |
| 2-ME: | 2-mercaptoethanol |
| D-GL-Antigen: | conjugate of D-GL and an antigen |
| AgE | Ragweed Antigen E |
| AgE-D-GL | conjugate of ragweed antigen E with D-GL |
| Sephadex | Epichlorohydrin cross-linked dextran gel of standardized quality and characteristics obtained from Pharmacia Fine Chemicals AB. SEPHADEX is a trademark. Sephadex G-25 has a water regain value of 2.5, and Sephadex G-100 has a water regain value of 10. (SEPHADEX PROPERTIES, Pharmacia Fine Chemicals) |
| Sepharose | Agarose modified according to the method of Hjerten by Pharmacia Fine Chemicals AB. Sepharose is a trademark. (PREPARATION OF SEPHAROSE, Pharmacia Fine Chemicals) |

BACKGROUND ART

Conjugates of low molecular weight haptens and a synthetic copolymer of D-glutamic acid and D-lysine (D-GL) have been shown to be very effective in inducing in experimental animals hapten-specific immunological tolerance which is highly specific and long-lasting (for review see Katz, 1974; Katz and Benacerraf, 1974). The tolerant state in such circumstances is (1) restricted to bone marrow-derived lymphocytes (B cells) which are precursors of antibody-secreting cells, (2) accompanied by a significant diminution of hapten-specific antigen-binding B cells, and (3) results in a preferential depression of the high affinity anti-hapten antibody response. Antibody responses of all immunoglobulin classes, including reaginic (IgE) antibodies responsible for local and systemic allergic reactions, are abolished by hapten-D-GL conjugates. Moreover, a very important aspect of this system is that such D-GL conjugates are highly effective in turning off ongoing antibody responses in previously sensitized individuals.

This system has been well-characterized with 2,4-dinitrophenyl (DNP)-D-GL (Katz, 1974; Katz and Benacerraf, 1974) and has been extended to the induction of tolerance to nucleoside conjugates of D-GL (Eshhar et al., 1975) which has clinical potential for abolishing anti-nuclear antibody production occurring in patients with systemic lupus erythematosus. Induction of tolerance to the major allergenic determinant of penicillin, the benzylpenicilloyl (BPO) hapten, has also been demonstrated by administering BPO-D-GL to experimental animals (Chiorazzi et al., 1976); the latter system has obvious clinical applicability in terms of treating patients with penicillin allergy. Based on the previously established knowledge in tolerance systems using hapten-D-GL conjugates, it is conceivable that larger macromolecules coupled to D-GL will have similar tolerance-inducing properties, once bound to specific immunoglobulin receptors on B lymphocytes. Therefore, I have been attempting to develop the methadology for preparation of stable conjugates of complex proteins coupled to D-GL for therapeutic use.

There are two major concerns in the preparation of protein-D-GL conjugates which will be tested in experimental animals for their biological activities and clinical applicabilities. (1) The conjugation reaction should be as mild as possible so that the antigenic determinants of the protein of interest are maximally retained. (2) The conjugate should be free of non-conjugated protein, especially protein dimers or oligomers which may be produced under the conjugation conditions and may not be easily separable from the conjugate by conventional chromatographic techniques. For all the protein-D-GL conjugates prepared, there should be a method to demonstrate conclusively the absence of non-conjugated protein, since contamination of any preparation by such molecules would pose a serious detriment to the effectiveness of tolerance induction and, more importantly, could constitute a life-threatening health hazard if such preparations were employed clinically.

Most commonly used coupling reagents such as glutaraldehyde, bisimidoesters, toluenediisocyanate and carbodiimides are not suitable for our purpose since they react mainly by coupling amino group with amino or carboxyl group and can result in extensive self-coupling of proteins. D-GL, which has an abundance of amino and carboxyl groups is particularly susceptible to this process. The ideal coupling method involves the introduction of a functional group into the protein (or D-GL) which reacts only with another functional group introduced into D-GL (or the protein). The recently reported coupling reagent m-maleimidobenzoyl-N-hydroxysuccinimide ester (MBS), Kitagawa and Aikawa, 1976) seems to be just such a reagent. Sulfhydryl groups, the other necessary reactive component, can be incorporated into D-GL (or protein) by known procedures.

Protein conjugates with D-GL are prepared by, first, preparing MBS modified protein and SHA modified D-GL and reacting MBS modified protein with SHA modified D-GL to produce protein-D-GL conjugates, and, conversely, by preparing SHA modified protein and MBA modified D-GL and reacting SHA modified protein and MBA modified D-GL to form the same class of protein-D-GL conjugates. In a preferred embodiment of the invention, MB-Antigen and SH-D-GL are reacted to form D-GL-Antigen conjugate, or conversely, SH-Antigen and MB-D-GL are reacted to form the same class of D-GL-Antigen conjugate. Specific novel methods for carrying out the preparation of MB-protein, SH-protein, MB-D-GL and SH-D-GL and reacting MB-protein with SH-D-GL or SH-protein with MB-D-GL to form the D-GL-protein conjugate are specific features of the invention. More particular, individual exemplary features of the invention are the preparation of MBS modified antigens such as MB-In, and MB-E, SHA modified antigens such as SH-In and SH-E, and MB-D-GL or SH-D-GL followed by the reaction of one of the MB-Antigens with SH-D-GL or one of the SH-Antigens with MB-D-GL to prepare D-GL-Antigen, e.g., D-GL-E or D-GL-In conjugates of, respectively, Ragweed antigen E or insulin.

Preparation and isolation of protein-D-GL conjugates, demonstrated by the exemplary OVA-D-GL conjugates, by the generation of SH-D-GL (biotin) from its protected precurser in situ in the presence of MB-Protein, and the purification by direct application of the reaction mixture to an avidin-Sepharose column are additional features of the present invention.

Other features of the invention include the specific reaction conditions, preparation and separation techniques and methods described in detail hereinafter.

It is pointed out that the OVA-D-GL conjugate system, the starting and intermediate reagents, and the reactions using ovalbumin, and the information related to these reactions, materials and procedures, are set forth in detail to exemplify the invention and not as a statement or implication of the scope of the invention. The invention is a general method for forming protein-D-GL conjugates. A particular application of the invention is the preparation of D-GL-Antigen conjugates. Ovalbumin reactions typify protein reactions and, therefore, are selected as illustrative only of a general invention.

BRIEF DESCRIPTION OF THE DRAWINGS

FIG. 9 graphically depicts the antigen E-D-GL induction of tolerance in the IgE antibody calss when administered to CAF$_1$ mice one year after initial sensitization with antigen E. Normal CAF$_1$ mice were exposed to 250 R whole body X-irradiation shortly prior to primary immunization with 10 μg of RAG in 4 mg of alum. All mice were bled on days 10 and 20 after sensitization and the levels of IgE anti-AgE antibodies are illustrated in the left panel. These mice were then left to rest for an interval of one year at the end of which they were bled for determinations of residual levels of IgE anti-AgE antibodies (also indicated in the left panel). These mice were then divided into 3 groups of which 2 were given 4 injections (i.d. or i.p. as indicated in the left panel), each consisting of either unconjugated AgE (75 μg) or AgE-D-GL (250 μg D-GL containing 75 μg AgE). The injections were given daily intervals. Five days after the final injection, these 2 treated groups and a third group of untreated control mice were then challenged with 5 g of AgE in 4 mg of alum. The IgE anti-AgE antibody responses of groups of 3 mice each are presented in the right panel as percent of the control response developed by untreated mice, with the actual control values illustrated in parentheses above or below the corresponding data point after secondary challenge.

BEST MODE FOR CARRYING OUT THE INVENTION

Reagents

Figure 1:
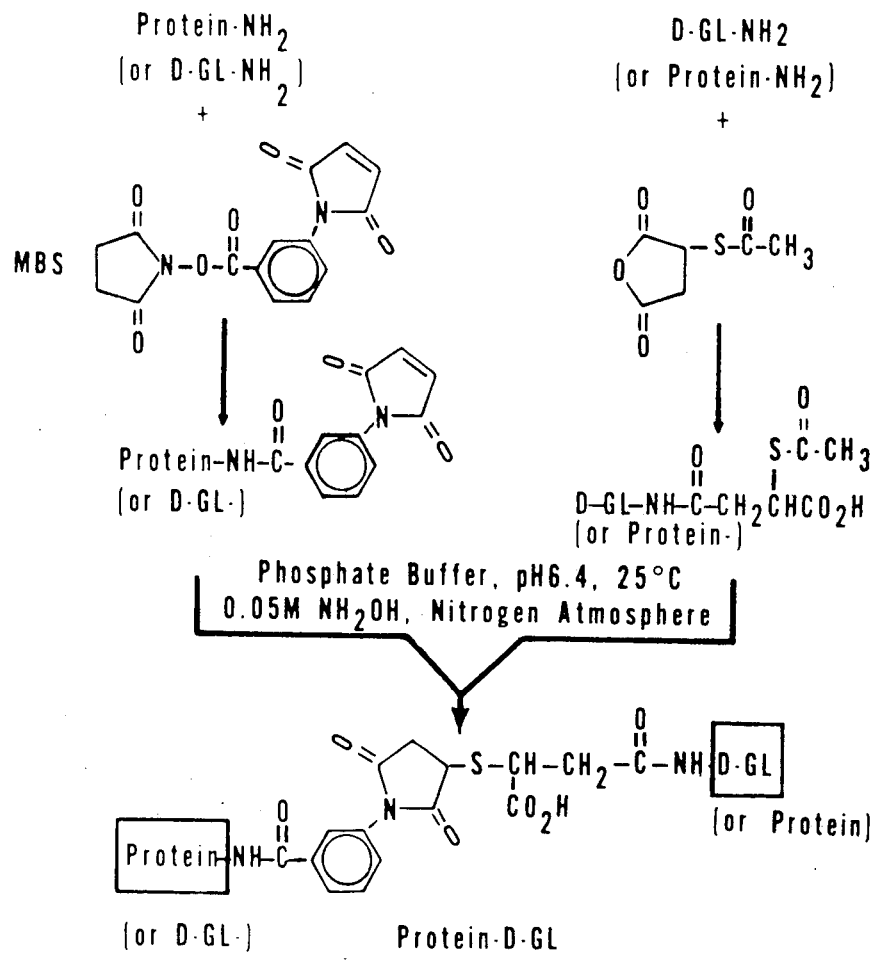
FIG. 1 is a flow chart which depicts the chemical coupling of protein to D-GL using protein (or D-GL) conjugates with a maleimide group and thiolated D-GL (or protein)

The random copolymer of D-glutamic acid and D-lysine (poly (D Glu$^{60}$D Lys$^{40}$) or D-GL) was obtained from Miles Laboratories, Inc., Elkhart, IN as the HBr salt and used as received. The polymer had an average molecular weight of 63,000 and a ratio of D-glutamic acid to D-lysine residues of 60:40. Hen egg ovalbumin (OVA), 5x recrystallized, was purchased from Pentex, Inc., Kankakee, IL. Insulin (porcine) was obtained from Schwarz/Mann, Orangeburg, NY. m-Maleimidobenzoyl-N-hydroxysuccinimide ester (MBS) and N-succinimidyl-e-(4-hydroxyphenyl) propionate were obtained from Pierce Chemical Co., Rockford, IL. S-acetylmercaptosuccinic anhydride, avidin and d-biotin were purchased from Sigma Chemical Co., St. Louis, MO. 5,5'-Dithiobis-(2-nitrobenzoic acid) was obtained from Calbiochem, La Jolla, CA. d-[Carbonyl-$^{14}$C] biotin was obtained from Amersham/Searle Co., Chicago, IL. Biotinyl-N-hydroxysuccinimide ester and [carbonyl-$^{14}$C] biotinyl-N-hydroxysuccinimide ester were prepared from d-biotin and d-[carbonyl-$^{14}$C] biotin, respectively, as described (Bayer and Wilchek, 1974; Jasiewicz et al., 1976).

Preparative Procedures

The amount of unmodified D-GL below refers to the weighed amount and the amount of unmodified protein is determined by uv absorbance.

A. Radiolabeling of D-GL, OVA, Insulin and Ragweed E

In order to radiolabel D-GL with $^{125}$I, the synthetic copolymer was substituted with hydroxyphenylpropionyl (HPP) as follows: 10 mg (157 nmol) of D-GL was dissolved in 1 mL of 0.075 M borate buffer, pH 8.5, and the pH of the solution was adjusted to 8.5. Fifty microliters of a solution of N-succinimidyl-3-(4-hydroxyphenyl) propionate (4 mg/mL, 760 nmol) in dimethylformamide was added and the mixture was stirred for 30 min. at room temperature. The resulting HPP-substituted D-GL was dialyzed extensively against phosphate-buffered saline (PBS, 0.01 M phosphate buffer, 0.15 M NaCl, pH 7.2). Using $\epsilon$ (280 nm)=1660 M$^{-1}$cm$^{-1}$ for 3-(4-hydroxyphenyl) propionamide (in PBS, pH 7.2), the molar quantity of the hydroxyphenylpropionyl group was determined. HPP$_4$-D-GL was radiolabeled with $^{125}$I using the standard chloramine-T oxidation procedure (Greenwood et al., 1963). The specific activity of the sample was 420 μCi/mg.

OVA and Insulin was labeled with $^{131}$I by the solid-phase lactoperoxidase method (David, 1972; David and Reisfeld, 1974). The specific activities were 2 mCi/mg and 5 mCi/mg, respectively. Ragween Antigen E is labeled with $^{131}$I in the same manner.

B. m-Maleimidobenzoyl-Ovalbumin (MB-OVA)

The maleimide group was incorporated into OVA by reacting the protein with m-maleimidobenzoyl-N-hydroxysuccinimide ester (MBS, Kitagawa and Aikawa, 1976). OVA (17 mg, 380 nmol) was dissolved in 1.0 mL of 0.01 M phosphate buffer at pH 7.0. Fifty μL of a solution of MBS (24.8 mg/mL, 4 μmol) in dimethylformamide was added. After stirring at room temperature for 30 min, the mixture was applied to a 0.9 cm×40 cm column of Sephadex G-25 (Pharmacia, Piscataway, NJ) equilibrated with 0.1 M phosphate buffer, pH 6.0 and eluted with the same buffer at 4° C. Collected fractions were monitored for absorbance at 280 nm and those containing the derivatized OVA were pooled and used directly for the conjugation reaction. In order to determine the quantity of maleimide group incorporated, an aliquot (100 μL containing 9 nmol of protein) of the solution was taken, flushed with nitrogen, and reacted with known amount of deoxygenated aqueous solution of 2-mercaptoethanol (2-ME, 25 μL, 35 nmol) for 20 min. Deoxygenated 0.2 M Tris-buffer, pH 8.2 (1 mL) and 0.01 M 5,5'-dithiobis(2-nitrobenzoic acid) in deoxygenated methanol (100 μL) was added and the color developed in the sample after 30 min. was measured at 412 nm on a Beckman model 25 spectrophotometer (Ellman's method, Ellman, 1959). The molar quantity of maleimide groups present then equals the molar quantity of 2-ME consumed. The amount of derivatized OVA in the aliquot was determined by Folin-Lowry method (Lowry et al., 1951) using OVA as the standard and the ratio of maleimide groups to OVA was found to be 2.4:1 (i.e. MG$_{2.4}$-OVA).

C. m-Maleimidobenzoyl-D-GL (MB-D-GL)

This compound was prepared essentially as described for MB-OVA, radio-labeled D-GL was used as a tracer. The buffer used to dissolve D-GL was 0.2 M phosphate buffer, pH 7.2 and the molar ratio of MBS to D-GL used in the reaction was 5:1. The molar quantity of maleimide groups was similarly determined and the derivatized D-GL was quantitated by radioactivity. The MB: D-GL ratio was found to be 2.4:1 (MB$_{2.4}$-D-GL).

D. m-Maleimidobenzoyl-Insulin (MB-In)-Ragweed Antigen E (MB-AgE).

MB-In was prepared essentially as described for MB-OVA except that the eluent used for the Sephadex G-25 was PBS (pH 7.2). Reaction of insulin (1 mM) with 5 mol-equivalent of MBS gave MB$_{0.9}$-insulin. MB-AgE was prepared by reacting 20 mg (540 nmol) of antigen:E and 4.2 mg (13.5 μmol in 200 μl of dimethylformamide)

of MBS in 2.0 ml of 0.01 M phosphate buffer, pH 7.0, and isolated by gel filtration chromatography on a column of Sephadex G-25, essentially as described for MB-OVA. The MB:AgE ratio was determined to be 3.6:1.

E. Mercaptosuccinyl-D-GL (SH-D-GL)

Thiolation of D-GL was effected by the reported method (Klotz and Heiney, 1962) of thiolation of proteins at the $\epsilon$-amino groups of lysine residues. D-GL (40 mg, 627 nmol, containing trace quantities of $^{125}$I-D-GL) was dissolved in 900 $\mu$L of 0.125 M phosphate buffer, pH 7.2, and the pH of the solution was adjusted to 7.2 with 1 N NaOH. Twenty $\mu$L of a solution of S-acetylmercaptosuccinic anhydride (12 mg/mL, 1.4 $\mu$mol) in dimethylformamide was added and the mixture was stirred at room temperature for 30 min., during which time the pH was maintained at 7.0 by the addition of 1 N NaOH. The solution was applied to a Sephadex G-25 column (1 cm $\times$ 23 cm) equilibrated with PBS, 0.01 M in Na$_2$EDTA and was eluted with the same buffer at 4° C. Effluent (4 mL) containing the derivatized D-GL ($^{125}$I) was collected and deoxygenated by three cycles of vacuum-bleeding in nitrogen. Deoxygenated 0.5 M hydroxylamine, pH 7.3 (400 $\mu$L), was added and the solution was incubated at 37° C. for 20 min. to remove the protecting acetyl group. The sulfhydryl groups present were quantitated by Ellman's method as described above (Ellman, 1959). The amount of the derivatized D-GL in the aliquot was determined by the radioactivity and the SH:D-GL ratio was found to be 1.2:1 (SH$_{1.2}$-D-GL).

SH$_{1.9}$-D-GL was similarly prepared by using a molar ratio of S-acetylmercaptosuccinic anhydride to D-GL of 5:1.

F. Mercaptosuccinyl-OVA (SH-OVA)

This compound was prepared essentially as described for SH-D-GL. The molar ratio of S-acetylmercaptosuccinic anhydride to OVA used in the reaction was 8.6:1. The ratio of sulfhydryl groups to OVA in the product was 1.1:1 (SH$_{1.1}$-OVA).

G. Biotin-D-GL

One hundred mg of D-GL (1.57 $\mu$mol) containing trace quantities of $^{125}$I-D-GL was dissolved in 3 mL of 0.05 M phosphate buffer, pH 7.2. The pH was adjusted to 7.2 with 1 N NaOH and 500 $\mu$L of a solution of biotinyl-N-hydroxysuccinimide ester (5.3 mg/mL, 7.84 $\mu$mol) in dimethylformamide was added. The mixture was stirred at room temperature for 2 h and was dialyzed against PBS and then against distilled water and finally lyophilized. The recovery (based on $^{125}$I counts) was generally 90–95%.

Utilizing [Carbonyl-$^{14}$C] biotinyl-N-hydroxysuccimide ester (and no $^{125}$I-D-GL), it was found that 90±% radioactivity was incorporated under the same condition as described above. Therefore, the ratio of biotin groups to D-GL in the product must be about 4.5:1.

H. Mercaptosuccinyl-D-GL-Biotin (SH-D-GL-Biotin)

This compound was prepared from biotin$_{4.5}$-D-GL as described for SH-D-GL.

I. Preparation of Avidin-Sepharose Conjugates with Reduced Affinity for Biotin Avidin-Sepharose conjugate was prepared by coupling 50 mg of avidin with 5 g of cyanogen bromide-activated Sepharose 4B (Pharmacia) in 15 mL of 0.1 M NaHCO$_3$ and 0.5 M NaCl, pH 8.3 for 16 h at 4° C. as described in the Pharmacia booklet (Affinity Chromatography Principles and Methods). A suspension of the conjugate in PBS was poured into a column. To dissociate the tetramer of avidin and remove non-covalently bound subunits, the column was eluted with 30 mL of 6 M guanidinium chloride and left at room temperature overnight followed by elution with 6 M guanidinium chloride until the effluent had A$_{280}$<0.01 (30 mL sufficed) (Green and Toms, 1973). The column was re-equilibrated in PBS (40 mL) and all the binding sites were saturated by equilibrating with 1.2 mM biotin in PBS (40 mL). Elution with 0.1 M glycine-HCl, pH 2.0 (40 mL), then removed the biotin from low affinity binding sites and the column was finally re-equilibrated in PBS for use (15 mL packed bed).

The capacity of the modified avidin-Sepharose was determined as follows: One mL (packed volume) of the gel was poured into a small column and an excess of [Carbonyl-$^{14}$C]-biotin with known specific activity was added. The column was eluted with PBS (5 mL) to remove unbound [$^{14}$C]-biotin. The bound [$^{14}$C]-biotin was then eluted with PBS containing biotin (1.2 mM) and was quantitated by the radioactivity. The capacity of avidin-Sepharose was 10.3 $\mu$g (42.2 nmol) biotin/mL gel. Using biotin$_{4.5}$-D-GL-$^{125}$I in place of [$^{14}$C]-biotin, the capacity was determined to be 0.5 mg (7.8 nmol) biotin$_{4.5}$-D-GL/mL gel.

J. Preparation and Isolation of OVA-D-GL (Biotin)

MB$_{2.4}$-OVA (30 mg, 667 nmol) in 3.0 mL of 0.1 M phosphate buffer, pH 6.0 was mixed with acetyl-S$_{1.9}$-D-GL-Biotin$_{4.5}$ (36 mg, 565 nmol, containing a trace quantity of $^{125}$I-labeled molecules) in 3.8 mL of PBS, 0.01 M in EDTA (pH of the mixture 6.4). The mixture was deoxygenated by three cycles of vacuum-bleeding in nitrogen. To the solution was added 680 $\mu$L of deoxygenated 0.5 M hydroxylamine, pH 7.3, and the mixture was stirred under nitrogen at 25° C. for 2.5 h. 2-Mercaptoethanol was added to a final concentration of 1 mM followed by N-ethyl maleimide to a final concentration of 2 mM. The solution was stirred at 25° C. for 20 min. after addition of each reagent.

One-third of the reaction mixture was applied to a column of avidin-Sepharose (40 mL packed bed) equilibrated with PBS at 4° C. and eluted with 100 mL and finally 80 mL of 0.1 M glycine-HCl, pH 2.0. The column was then equilibrated with PBS for reuse. The effluents were monitored for $^{125}$I radioactivity and uv absorbance at 280 nm.

The biotin-eluted fractions were dialyzed to remove free biotin and were concentrated either by Amicon ultrafiltration or lyophilization (see Results section for quantitation).

K. Preparation of D-GL-In and D-GL-AgE (Biotin)

Insulin-D-GL (Biotin) was similarly prepared by reacting MB$_{0.9}$-Insulin (59 $\mu$M) and acetyl-S$_{1.2}$-D-GL-Biotin$_{4.5}$ (47 $\mu$M) in PBS. Ragweed-D-GL (Biotin) was prepared by reacting MG$_{3.6}$-AgE (16 mg, 433 nmol in 3.6 ml of 0.1 M phosphate buffer, pH 6.0) and SH$_{1.9}$-D-GL-Biotin$_{4.5}$ (30.6 mg. 480 nmol, containing trace quantity of $^{125}$I-labeled molecules, in 3.13 ml of PBS, 0.01 M in EDTA) and isolated by affinity column chromatography on avidin-Sepharose, essentially as described for OVA-D-GL. A product composed of conjugated AgE and total D-GL in a ratio of 0.5:1 was obtained as quantitated by the same method used for OVA-D-GL. The conjugate generally retained 10–20% antigenicity of antigen E as determined by the percentage of the conjugated protein adsorbed by anti-AgE-Sepharose immunoadsorbent.

L. Antisera

Rabbit anti-OVA antiserum was obtained by hyperimmunization of New Zealand red rabbits with 50–100 µg of OVA emulsified initially in complete Freund's adjuvant and subsequently in incomplete Freund's adjuvant administered subcutaneously. Rabitt anti-insulin antiserum was prepared by hyperimmunication of the same kind of rabbits first with 200 µg of insulin-KLH in complete or incomplete Freund's adjuvant as above and then with 200 µg of insulin-KLH in 4 mg of alum, administer intraperitoneally.

M. Immunoadsorbent Affinity Chromatographic Column

The conjugate of OVA with Sepharose 4B was prepared by reacting OVA with cyanogen-bromide activated Sepharose 4B (Pharmacia). The column was washed with 0.1 M glycine-HCL, pH 2.2, until $A_{280} < 0.005$ before each use.

Antibodies with affinity for OVA were isolated by passing rabbit anti-OVA antiserum through OVA-Sepharose and eluting with 0.1 M glycine-HCl, pH 2.2, after washing with PBS. The acid-eluted solution was neutralized with solid Tris (hydroxylmethyl) aminomethane and dialyzed first against PBS and then 0.1 M $NaHCO_3$, 0.15 M NaCl, pH 8.3. The solution was used directly to conjugate with cyanogen-bromide activated Sepharose 4B to give an immunoadsorbent with affinity for OVA. The column was washed with 0.1 M glycine-HCl, pH 2.2, before each use.

Immunoadsorbent with affinity for insulin was similarly prepared from anti-insulin antibodies isolated from rabbit anti-insulin serum by insulin-Sepharose column.

Amino Acid Analysis

Amino acid analyses were made on a Beckman Spinco Model 121-M amino acid analyzer; protein samples were hydrolyzed in 6 N HCl in sealed and evacuated tubes at 110° C. for 24 h.

Modification of OVA and D-GL: General Considerations

A summary of the preparative reactions employed in this study is presented in FIG. 1. This approach is discussed in the following sections.

A. Maleimidobenzoylation

Early in these studies, it was found that the maleimide group on MB-OVA and MB-D-GL was not stable at neutral pH. The maleimide content gradually decreased, most probably by reacting with the ε-amino group of lysine residues. This was especially noticeable on D-GL which has an abundance of such amino groups. The half-life of the maleimide group on D-GL was found to be only a few hours at room temperature at pH 7.0. The reaction of maleimide derivatives with amines has been reported in the literature (Smyth et al., 1960). The maleimide group on MB-OVA and MB-D-GL was found to remain intact longer at lower pH, i.e. pH 6.0. Less than 10% of the maleimide groups on the modified OVA and D-GL reacted in one hour at room temperature at pH 6.0. It was therefore essential that the gel filtration be run at pH 6.0, in the cold, and the sample be subsequently kept at the same pH. In addition, care was taken to prepare the compound just before the conjugation reaction.

When the maleimide group is incorporated into an OVA molecule, both amino groups and sulfhydryl groups of OVA may react with the maleimide group either on the same or a different molecule. Therefore, dimerization of self-cross-linking is very likely. When MB-OVA was incubated at room temperature and at pH 6.2 for 2 hours (the OVA-D-GL conjugation conditions), around 10% of OVA was dimerized as determined from the uv absorbance of the peak eluted earlier than OVA on Sephadex G-100. This represents the maximum amount of dimerization which could occur in the OVA-D-GL conjugation reaction.

B. Thiolation

In the spectrophotometric determination of sulfhydryl groups by Ellman's method, it was found to be very important to deoxygenate the reaction solution as the reagent, 5,5'-dithiobis (2-nitrobenzoic acid), was rapidly oxidized in the buffer solution used (0.2 M Tris-buffer, pH 8.2) and produced color which interfered with the reading at 412 nm. Hydroxylamine seems to accelerate this oxidation and deoxygenation of the solution is especially important in its presence if the correct SH content is to be obtained. In stringently deoxygenated solution, hydroxylamine does not interfere with this spectrophotometric determination.

Oxidation of the sulfide (OVA or D-GL) to disulfide and, therefore, the resulting formation of protein and D-GL dimers was the major problem in the thiolation of OVA and D-GL. In an investigation on thiolation of D-GL, it was found that the succinylation reaction and the subsequent gel filtration on Sephadex G-25 did not have to be run under deoxygenated conditions; however, it was especially important that the solution be deoxygenated before hydroxylamine treatment. When SH-OVA was incubated at room temperature and at pH 6.2 for 2 hours, 26% of the protein was dimerized as determined by chromatography on a Sephadex G-100 column.

It was also found that hydroxylamine did not interfere with the reaction of the sulfhydryl group with the maleimide group and, therefore, did not have to be removed from the SH-OVA or SH-D-GL preparation prior to the conjugation reactions. As a matter of fact, generation of free sulfhydryl from the S-acetyl form can be performed in the presence of maleimide.

Thiolated OVA and D-GL werre stable if kept in the protected form (i.e. S-acetylated). For instance, it was found that acetyl-S-D-GL was stable for at least a week at 4° C.

Conjugation of OVA and D-GL

There are two alternatives to coupling OVA and D-GL by the maleimide-sulfhydryl coupling method: (i) Reaction of MB-OVA with SH-D-GL; (ii) Reaction of SH-OVA with MB-D-GL as illustrated in FIG. 1. In preliminary studies, $^{131}I$-labeled protein and $^{125}I$-labeled D-GL were used as tracers in order to facilitate identification of the conjugate since it would contain both the $^{125}I$ and $^{131}I$ radiolabels.

In each reaction, the two components were mixed and the reaction solution was incubated at room temperature and pH 6.2 for 2 hours under nitrogen atmosphere (solutions were deoxygenated by three cycles of evacuation-bleeding in nitrogen), and after 2 hours of reaction time, the unreacted sulfhydryl groups were blocked with N-ethylmaleimide (1 mM). The reaction solution in each case was applied to a Sephadex G-100 column. The fractions were counted for $^{125}I$ and $^{131}I$ radioactivity which was followed by a peak containing only $^{131}I$. The elution positions of D-GL and its conjugates were at the void volume, closer than would be expected based on their molecular weights. This is probably related to the non-globular nature of the D-GL molecule. In parallel experiments, in which modified OVA (MB-OVA or SH-OVA) was incubated alone under the conjugation conditions and was subjected to gel filtration on Sephadex G-100, it was found that the elution position of the OVA dimers (and oligomers) formed was close to that of D-GL and the conjugate. Therefore, the first peak contained a mixture of the OVA-D-GL conjugate, D-GL and OVA dimers (and oligomers), and, for absolute purifications, I resorted to other methods such as affinity chromotography.

In both approaches, about the same amount of protein reacted as indicated by the ratio of the $^{131}I$ counts in the first and second peaks of Sephadex G-100 column. However, the approach (i) is probably a better choice since it should result in less protein self-coupling as indicated in previous sections. Another possible method of conjugating OVA with D-GL is to couple MB-D-GL to unmodified OVA using the naturally-occurring sulfhydryl group of OVA. When equimolar amounts of MB-D-GL and OVA were reacted, the conjugate was formed only in low yield. In this experiment, we did not use radiolabeled OVA as tracer since the sulfhydryl group of OVA is very likely converted to sulfenyliodide upon radiolabeling (Cunningham and Nuenke, 1961). The conjugated protein in the first peak of the Sephadex G-100 column was quantitated by Lowry-Folin method (see below for quantitation methods).

Preparation and Isolation of Biotin-labeled OVA-D-GL Conjugate

The preparation procedures for OVA-D-GL (biotin) from MB-OVA and SH-D-GL (biotin) was described in the Materials and Methods. One feature of this preparation is the generation of SH-D-GL (biotin) from its protected precursor in situ in the presence of MB-OVA. The extent of self-coupling of SH-D-GL was thereby reduced and the overall preparative procedure was simplified. Another feature of the preparation is the direct application of the reaction mixture to the avidin-Sepharose column for purification.

Figure 2:
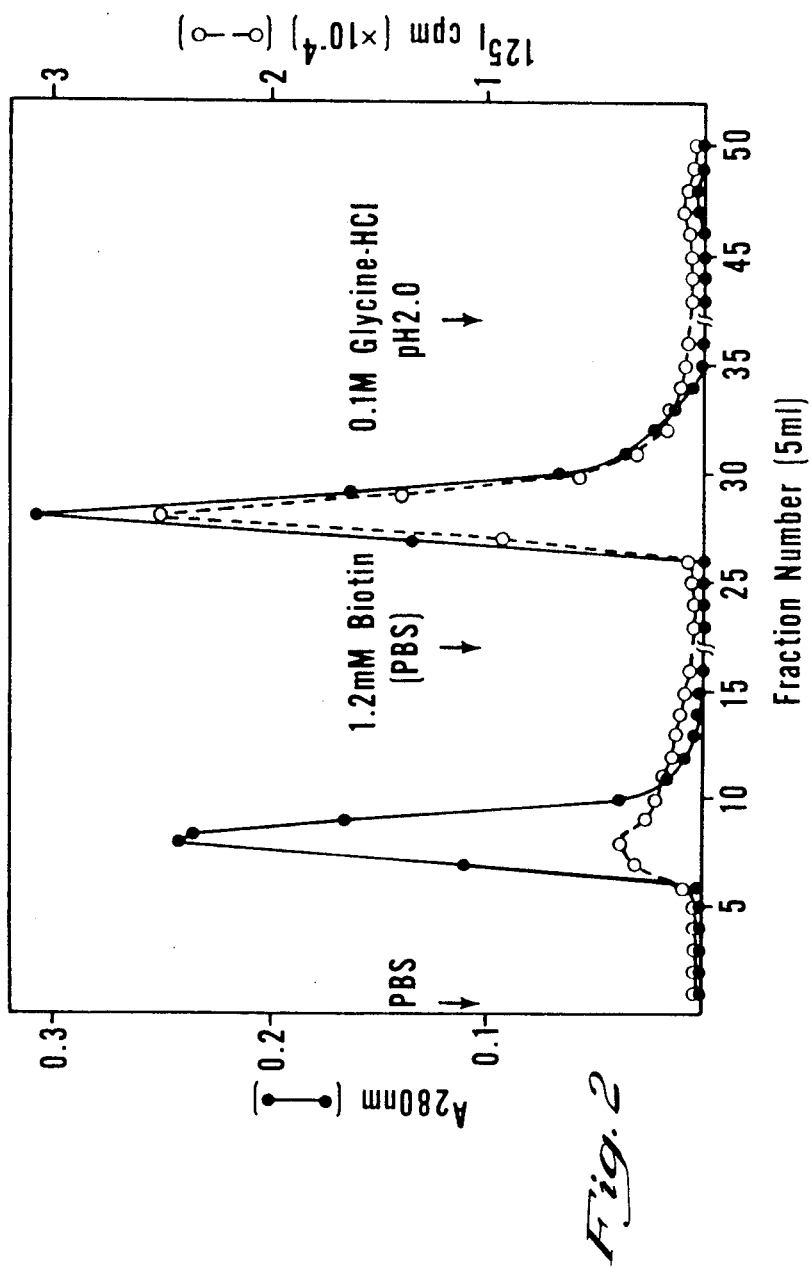
FIG. 2 is a graphical depiction of the purification of biotin-labeled OVA-D-GL conjugate by affinity chromatography on avidin-Sepharose. Conjugate preparation composed of 9.9 mg (220 nmol) of OVA and 11.9 mg (187 nmol) of D-GL was loaded on the column of avidin-Sepharose (40 mL) equilibrated with PBS at 4°. Arrows indicate change of eluent. Flow rate 57 mL/h.

The separation profile is shown in FIG. 2. The fractions were monitored for radioactivity and uv absorbance at 280 nm. Elution with PBS alone gave a peak which consisted of a mixture comprised of (1) unconjugated OVA and/or OVA dimers and aggregates; and (2) unconjugated D-GL or OVA-D-GL conjugates which either lacked biotin or in which the biotin molecules were unexposed for binding to avidin. Elution with PBS containing biotin (1.2 mM) then yielded the desired OVA-D-GL (biotin) conjugate together with unconjugated D-GL (biotin). Further elution with 0.1 M glycine-HCl, pH 2.0 yielded little material. The first peak contained 15% of the $^{125}I$ counts loaded on the column. The second peak contained 70% of the counts and third peak 5%. Therefore, the total recovery was about 90%.

Figure 3:
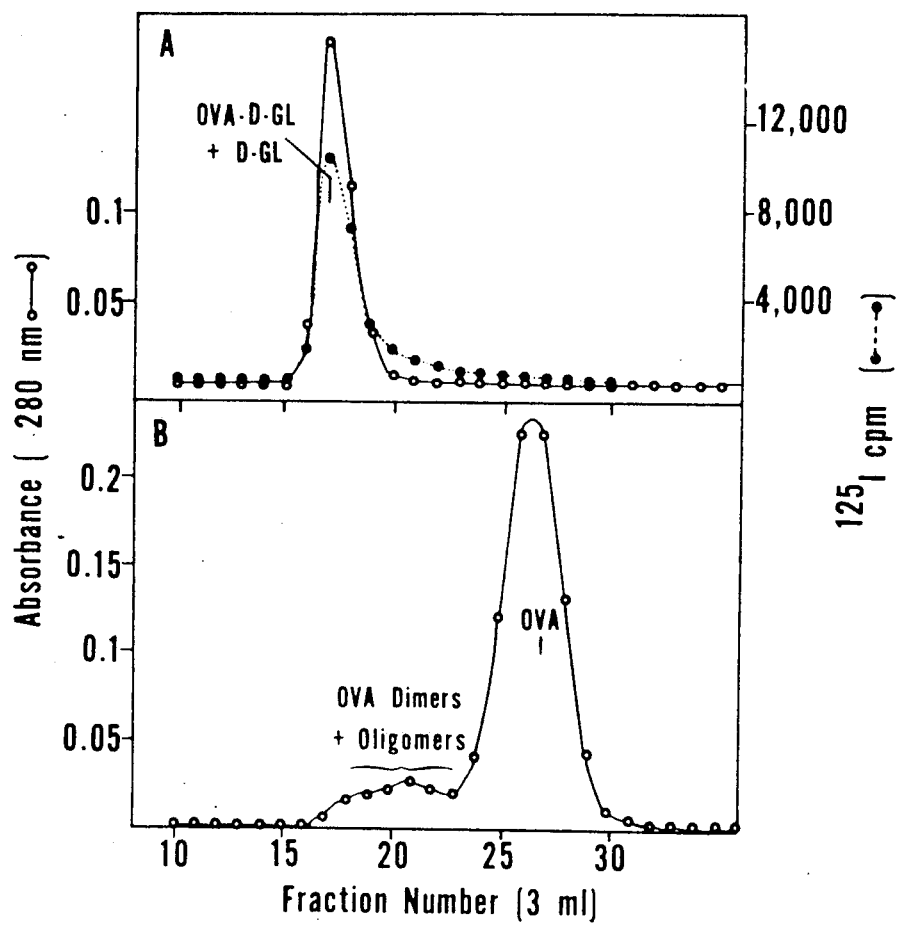
FIG. 3 is a graphical depiction of: (a) Sephadex G-100 chromatography of biotin-eluted material from avidin-Sepharose column (FIG. 2, second peak); and (b) Sephadex G-100 chromatography of PBS-eluted material from avidin-Sepharose column (FIG. 2, first peak). The column (1.6 cm×80 cm) was equilibrated with PBS and eluted with the same solvent at 4°. Flow rate 9.6 mL/h.

The effectiveness of the avidin-Sepharose column for purification of OVA-D-GL conjugate is demonstrated in FIG. 3. Material eluted by PBS was fractionated on Sephadex G-100 (FIG. 3B) and was shown to contain mainly OVA and its dimer (eluted at positions identical to that of products obtained when MB-OVA was allowed to stand at room temperature for 2 h). Material eluted by biotin-containing buffer was similarly shown to be exclusively devoid of unconjugated protein (FIG. 3A). It is to be noted that D-GL ($^{125}I$) exhibits long tailing on Sephadex G-100 (FIG. 3A). Since dinitrophenylated D-GL (DNP$_{10}$-D-GL) did not exhibit such long tailing (fractions monitored by absorbance at 360 nm), this is probably due to fragmentation of D-GL molecules upon radioiodination or due to radiodecomposition of the radiolabeled D-GL (Bayly and Evans, 1966) although it is also partially due to the heterogeneity of D-GL employed.

Quantitation of Biotin-Containing Protein-D-GL Conjugate

For quantitation of OVA, we originally used $^{131}I$-labeled OVA as tracer and thought that the conjugate could be identified by the presence of both $^{125}I$ and $^{131}I$ counts precipitable by anti-OVA antibodies. However, we found that most (>70%) of the $^{131}I$ labels on OVA were not recovered from the avidin-Sepharose column. This is most probably due to the release of the labile radiolabels on OVA which are present as sulfenyliodide (Cunningham and Nuenke, 1961).

There is also a problem in the quantitation of protein in the conjugate preparation by Lowry-Folin method, since D-GL will give a Folin color. For example, a test solution (2.4 mL) containing a final concentration of 0.65 μM of D-GL has $A_{700}$ of 0.22 compared to $A_{700}$ of 0.75 for a solution of OVA (0.92 μM). The amount of protein can however be quantitated by the Lowry-Folin method (Lowry, et al. 1951) provided that the contribution from D-GL be corrected for. For example, the amount of color ($A_{700}$) developed in the tests for solutions containing 50 μg D-GL and varied amounts of OVA is linear for 0–100 μg of OVA and is equal to the sum of that for isolated D-GL and OVA.

Quantitation can be more conveniently done from uv absorbance of the conjugate. MBS-modified protein does not have the same absorbance as the unmodified protein since maleimidobenzoyl (MB) groups contribute to the absorption at 280 nm. The uv absorption of the conjugation reactions mixture was measured after the maleimide groups are quenched by mercaptoethanol. Since the reaction mixture contained known amount of protein derivatized with MB in which the maleimide moieties are saturated by coupling to SH on either D-GL or mercaptoethanol, an extinction coefficient for the modified protein can be calculated and the amount of conjugated protein obtained from the avidin-Sepharose column can thereby quantitated. Since proteins are probably not uniformly modified by MBS (i.e. number of MB groups on the modified proteins may follow a Poisson distribution (Gennis and Cantor, 1972), the absorbance used here is an average absorbance. It is also assumed that there is no significant difference in the 'average' absorbance between D-GL-conjugated and -purification methods.

Figure 4:
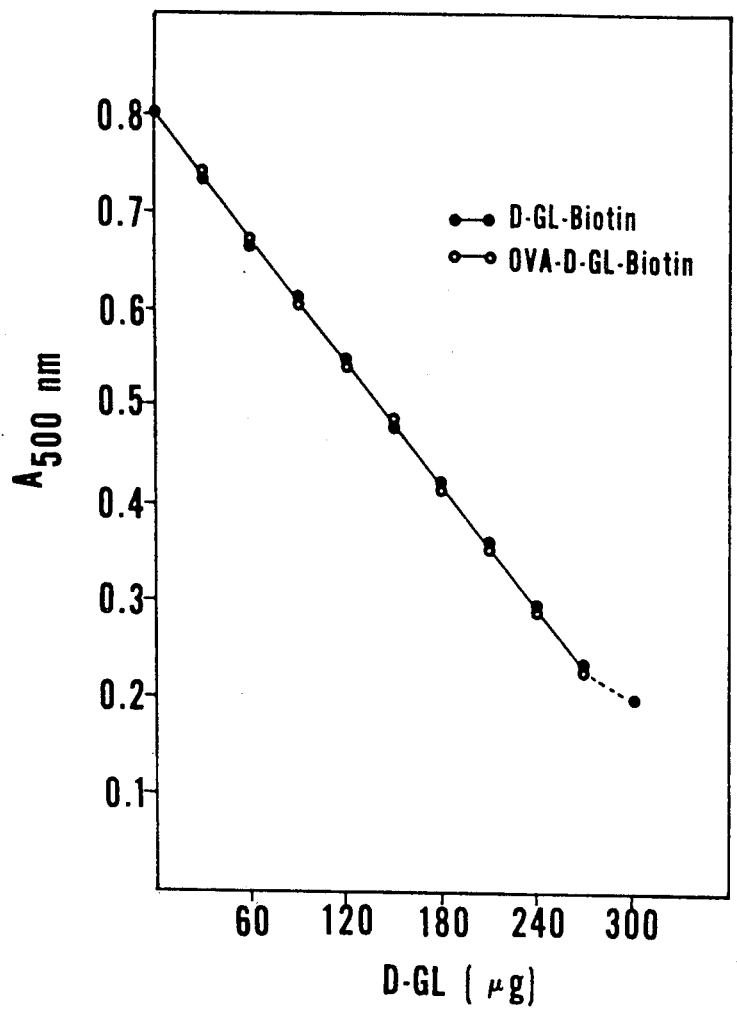
FIG. 4 is a graphical depiction of the spectrophotometric assay of biotin-labeled D-GL and OVA-D-GL conjugate. A 1 mL solution of avidin (8.3 $\mu$M) containing 4-hydroxyazobenzene-2'-carboxylic acid (HABA, 240 $\mu$M) was titrated with a solution (3 mg/mL) of biotin$_{4.5}$-D-GL (-o-o-) or a mixture of biotin$_{4.5}$-D-GL and biotin$_{4.5}$-D-GL-OVA containing an equal amount (3 mg/mL) of total biotin$_{4.5}$-D-GL (-o-o-)

During the development of the conjugation and purification methods reported here, $^{125}I$-labeled D-GL was always used to facilitate quantitation. Biotin-modified D-GL can also be quantitated by a sensitive spectrophotometric assay for biotin-containing compounds. It is based on the use of the dye 4-hydroxyazobenzene-2'-carboxylic acid which binds to avidin to form a complex having an absorption maximum at 500 nm. Biotin can displace this dye from avidin and cause a decrease in absorption at 500 nm which is linearly proportional to the concentration of biotin (Green, 1970). It was found that there was a linear relationship between the decrease of absorption and the amount of biotin-D-GL up to a maximum of 250 μg which corresponded to a $\Delta A_{500}$ of 0.55. It was also found that conjugation of protein to D-GL had little effect on the binding of the biotin on D-GL to avidin (FIG. 4). The amount of D-GL in the conjugate preparation can therefore be quantitated using biotin-D-GL as the standard.

Quantitated in these ways, a particular conjugate preparation obtained after avidin-Sepharose purification contained 11.0 mg (244 nmol) of conjugated OVA and 21.0 mg (330 nmol) of conjugated and non-conjugated D-GL, starting from 667 nmol of MB-OVA and 565 nmol of acetyl-S-D-GL. The sample was subjected to amino acid analysis to obtain a more accurate quantitation of conjugated protein. The results indicated that the actual amount of protein was less than that estimated as above with a difference of less than 10%.

Figure 5:
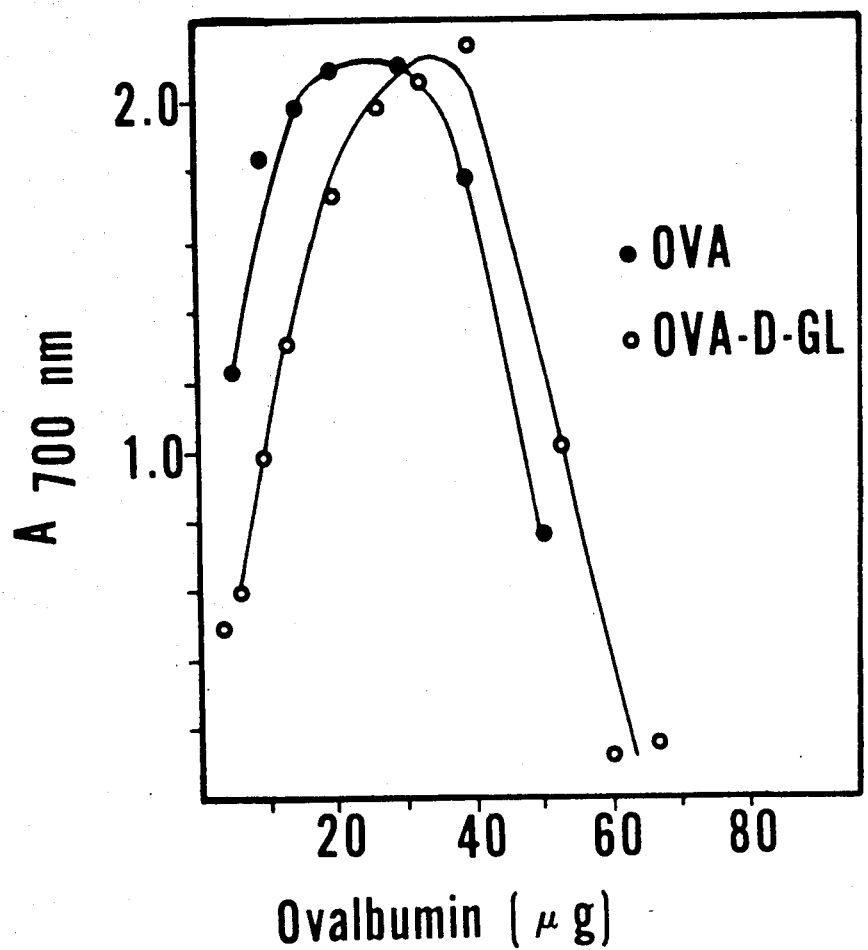
FIG. 5 is a graphical depiction of the quantitative precipitin reaction of OVA and OVA-D-GL conjugate with rabbit anti-OVA serum. Reactions were run with 200 $\mu$L of OVA or OVA-D-GL (the amount of OVA in the conjugate was determined as described in the text) and 100 $\mu$L of antiserum. The mixture was incubated at 37° for 1 h and 4° overnight. The precipitates were collected, washed with cold PBS, and analyzed by Lowry-Folin method.

Immunochemical Characterization of OVA-D-GL and Purification of the Conjugate by Immunoadsorbent Affinity Chromatography Quantitative precipitin reaction of OVA-D-GL preparation after the avidin-Sepharose purification with rabbit anti-OVA serum is shown in FIG. 5 which illustrates that the majority of antigenic determinants of OVA were retained after conjugation.

Protein-D-GL conjugates were further purified by immunoadsorbent affinity chromatography on columns prepared with anti-protein antibodies. The column was first eluted with PBS and the desired conjugate was recovered by elution with 0.1 M glycine-HCl buffer at pH 2.2. Conjugates were found to be stable under these purification conditions, since they could subsequently be quantitatively readsorbed by the immunoadsorbent after neutralization. When OVA-D-GL preparation was subjected to this purification, 76% of the protein was in the acid-eluted fractions as determined from absorbance at 280 nm. This represented the fraction of conjugated-OVA which retained the capacity to combine with antibodies. Together with the protein, 39±3% of D-GL (quantitated by $^{125}$I counts) were contained in the acid-eluted fractions. This represented the amount of D-GL conjugated to OVA which retained antigenicity. It was demonstrated that these immunoadsorbent columns do not have affinity for non-conjugated D-GL.

Preparation of Insulin-D-GL and Ragweed Antigen E Conjugates

The same conjugation and isolation procedures were applied to preparation of insulin-D-GL conjugate. The conjugate was similarly purified by avidin-Sepharose and anti-insulin immunoadsorbent columns. A preparation containing insulin and D-GL in a ratio of 0.8:1 (conjugated insulin:total D-GL) was obtained by reacting MB-insulin and SH-D-GL in concentrations desigated in Materials and Methods and then subjecting the conjugate to avidin-Sephrose purification.

Figure 6:
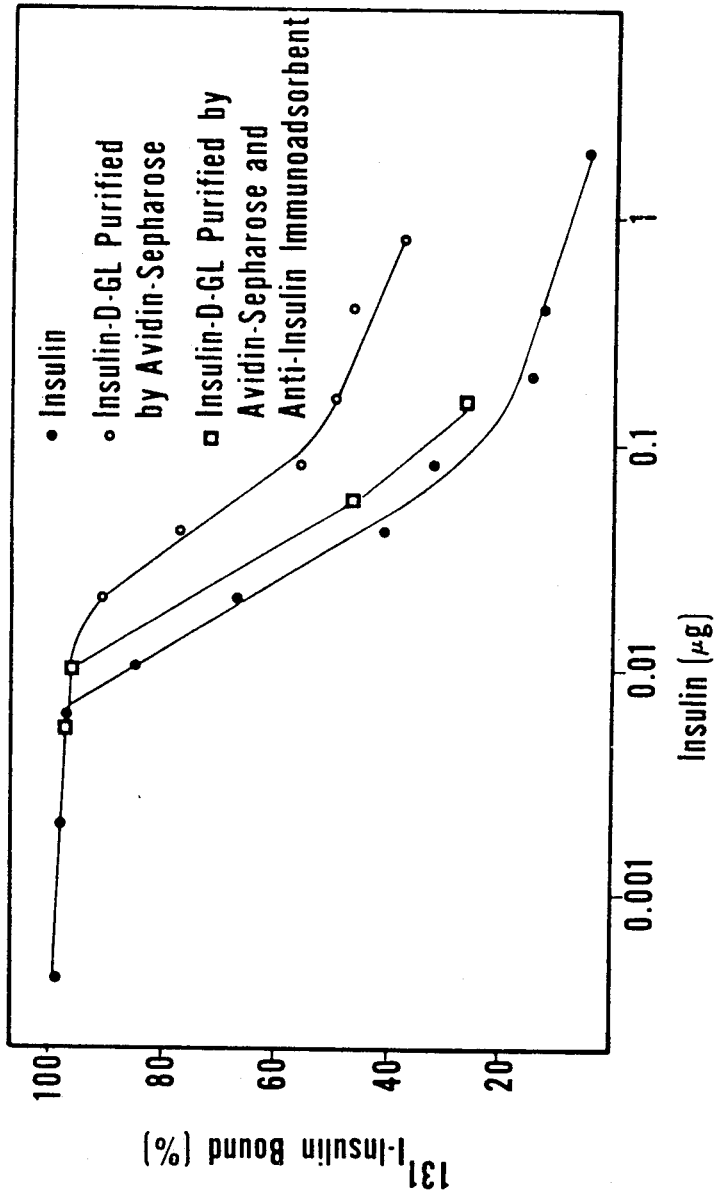
FIG. 6 is a graphical depiction of the results of the testing of insulin-D-GL antigenicity by insulin radioimmunoassay. Insulin (porcine) or insulin-D-GL was incubated with rabbit anti-insulin serum (1:40) at 4° for 1.5 h. $^{131}$I-insulin was added and the mixture was incubated at 4° for 1.5 h. Antigen-antibody complexes were precipitated with goat anti-rabbit $\gamma$-globulin and the supernatants were counted for $^{131}$I radioactivity. Triplicates were run for each concentration of antigen.

The affinity of D-GL-conjugated insulin for rabbit anti-insulin antibodies before and after immunoadsorbent purification was assessed by a radioimmunoassay essentially as described by Glover et al. (1967). The results are shown in FIG. 6. There is a substantial loss of antigenicity of insulin upon conjugation to D-GL. The percentage antigenicity one assesses from this radioimmunoassay depends on what percent-bound one chooses. At 50% bound, the antigenicity retained in 30%, in agreement with the percentage of insulin-D-GL adsorbed by anti-insulin column. After purification by anti-insulin immunoadsorbent, insulin-D-GL exhibited 68% of the antigenicity of insulin. The difference between the inhibition of $^{131}$I-insulin binding by insulin and by the purified insulin-D-GL here must be reflecting the difference in the affinity of two molecules for anti-insulin antibodies.

These same preparative techniques are applicable to the preparation of Ragweed antigen E-D-DG conjugates.

The coupling method employed is based on the reaction of a maleimide group conjugated to the protein (or D-GL) and a sulfhydryl group either present on the native protein or introduced into the protein (or D-GL) by thiolation (FIG. 1), as originally developed by other investigators (Kato et al., 1975, 1976; Kitawawa and Aikawa, 1976). Using OVA as a prototype protein, three different approaches were tested and it was demonstrated that conjugation by reacting MB-OVA and SH-D-GL was most satisfactory in terms of its higher efficiency and lower extent of protein self-coupling. Modified-OVA with an average of two to three maleimide groups and modified D-GL with an average of one to two sulfhydryl group were reacted in this conjugation reaction.

This method is extremely mild, has high coupling efficiency, and does not result in extensive self-coupling, intra- or intermolecular, of D-GL or protein as occurs when other commonly employed coupling reagents are used (such as glutaraldehyde, bisimidoesters, toluene diisocyanate and carbodiimides). However, it was found that dimerization of protein was still not totally avoidable since maleimide groups also react with amino and sulfhydryl groups of another protein molecule. Therefore, a method to separate protein dimers (and aggregates) from the conjugates was needed. Affinity chromatography is clearly the method of choise. Ideally, if antibodies specific for D-GL were available, we could use an anti-D-Gl immunoadsorbent as the affinity column. However, since D-GL is not immunogenic, this is not possible. In order to circumvent this problem, a method has been devised which applies the well-known affinity between a protein, avidin, and the small vitamin molecule, biotin. The use of biotin for this purpose, furthermore, would be consistent with sound and ethical medical therapeutic principles since its administration should be completely safe. Thus, biotin was introduced into the D-GL molecule to create a probe which allows the separation of the biotin-labeled protein-D-GL conjugate from non-conjugated protein by affinity chromatography on an avidin-Sepharose column.

The avidin-biotin complex is one of the tightest biological complexes known (for review, see Green, 1975). Due to its high affinity and specificity, this system has been applied in many biological studies (see references in Liu and Leonard, 1978). However, the application of avidin-Sepharose in the affinity chromatographic isolation of biotin-containing molecules has been limited, due to the problem in recovery since the affinity of avidin to biotin is so high. To circumvent this problem the avidin-Sepharose was modified in such a way that the biotin-labeled compounds can be recovered with high yields under very mild conditions and the affinity column can be easily recycled. A similar modification of avidin-Sepharose for the purification of biotin-containing enzymes has recently been reported (Maloy, 1977).

Using these methods, an OVA-D-GL (biotin) conjugate which is absolutely free of non-conjugated OVA was obtained. The ratio of OVA to D-GL was 0.7:1. These preparations consisted of the conjugate and the free D-GL-(biotin). It is to be noted that, since there is more than one sulfhydryl group and maleimide group on D-GL and OVA, respectively, molecules such as containing two OVA on one D-GL or two D-GL on one OVA are probably present. For present purposes, the free D-Gl-(biotin) does not have to be removed from the conjugate preparations since it has been well-established in this laboratory that D-GL is neither immunogenic nor toxic. Moreover, the introduction of small numbers of the vitamin molecule, biotin, should not induce any change in the non-immunogenic and nontoxic properties of D-GL.

Industrial Applicability

The methods which have been developed can be applied to the preparation of many protein-D-GL conjugates. In general, protein is modified with m-maleimidobenzoyl-N-hydroxysuccinimide ester to give MB protein which is reacted with SH-D-GL-biotin generated in situ from acetyl-S-D-GL by hydroxylamine. The reaction mixture is then subjected to avidin-Sepharose affinity chromatography to separate the conjugate and D-GL from protein dimers, oligomers or aggregates. The conjugate fractions can be further purified by immunoadsorbent affinity chromatography on a column prepared with anti-protein antibodies. This should remove the non-conjugated D-GL and any conjugate containing protein with disrupted antigenic determinants from the stable conjugate. Therefore, the application of avidin-biotin system has provided a convenient and rapid method for purification of our conjugates. More importantly, it has provided us with a way to obtain conjugates which are absolutely free of non-conjugated protein.

The conjugation and purification procedures have also been applied to insulin-D-GL. The efficiency of conjugation reaction is quite dependent on the protein employed. Insulin-D-GL was produced in high yield even though MB-insulin containing only an average of one maleimide group was used.

In this study, there was great concern about retention of antigenicity of proteins conjugated to D-GL. It should be also of general interest to see the effect of modification of proteins by a polymer containing large numbers of amino and carboxyl groups capable of interacting with proteins by electrostatic and hydrogen bonds on the capacity of the protein to combine with its antibodies. It was demonstrated that conjugation of OVA with D-GL does not affect its ability to form precipitating complexes with antibodies (FIG. 5). The shape of the quantitative precipitin reaction curve of OVA-D-GL is similar to that of OVA. The equivalence point is shifted to a higher antigen concentration for OVA-D-GL; this can be accounted for by the presence of some conjugates containing OVA with altered antigenic determinants which are non-precipitable by anti-serum and non-adsorbable by anti-OVA immunoadsorbent.

The effect of D-GL on the affinity of the D-GL-conjugated protein for its antibodies and the effect of purification by immunoadsorbent affinity chromatography are best demonstrated in the case of insulin-D-GL (FIG. 6). Insulin-D-GL prepared under the present conjugation conditions retained less than 30% of the antigenicity of insulin. This is not unexpected since antigenicity of insulin is very sensitive to chemical modifications. For example, modification of phenylalinine-B 1 amino group of insulin by acetylation or acetoacetylation causes a marked decrease of its affinity for anti-insulin immunoadsorbent, insulin D-GL exhibited substantial retention of the antigenic structure of insulin. These conjugates must have a D-GL conjugated at some specific site(s). It is interesting that antigenicity of insulin is not significantly disturbed by conjugation with a large molecule, such as D-GL, if it is appropriately conjugated. Since the present purification procedures guarantee the absence of any non-conjugated insulin, it will be of interest to test the hormonal activity of the conjugate.

Biologic Response

The results of these studies on the tolerogenic activity of OVA-D-GL in mice have indicated that the conjugate is, indeed, effective in suppressing reaginic (IgE) antibody responses. The capacity of such protein-D-GL conjugates to suppress specific antibody responses are of obvious significance to their clinical applicability for therapy in various allergic and autoimmune diseases.

Animals and Immunization $CAF_1$ mice (8–12 weeks old unless otherwise specified) were obtained from the Jackson Laboratories, Bar Harbor, ME, and were immunized and challenged intraperitoneally (i.p.) with 10 $\mu$g of OVA or 5 $\mu$g of AgE (or ragweed extract-RAG) adsorbed on $Al(OH)_3$ gel (alum, 4 mg or 2 mg) as described and according to experimental protocols as given in results, below.

Measurements of Antibodies

A. The concentration of IgE anti-OVA or anti-AgE antibodies were quantitated by passive cutaneous anaphylaxis (PCA) reactions in rats as described previously from this laboratory, with titers presented as reciprocals of highest dilutions yielding positive reactions.

B. The IgG antibody activity of mouse anti-OVA antisera was measured by solid-phase radioimmunoassay using $^{125}$I-labeled rabbit anti-mouse Fab. That of mouse anti-AgE antisera was determined by a double antibody method using $^{125}$I-labeled AgE and a rabbit anti-mouse serum.

OVA-D-GL Induces Persistent Tolerance in the IgE, but not the IgG, Antibody Class in $CAF_1$ Mice The three groups of normal $CAF_1$ mice were injected introdermally (i.d.) and intravenously (i.v) with 4 doses, administered at 2-day intervals, of either (1) OVA-D-GL containing 250 $\mu$g of total D-GL (100 g of conjugated OVA); (2) 100 $\mu$g of unconjugated OVA; or (3) a mixture of 250 $\mu$g of D-GL plug 100 $\mu$g of unconjugated OVA. One day after the 4th dose, these mice and a group of untreated control mice were primarily immunized with 10 $\mu$g of OVA plus alum (day 0). On day 15, mice were treated again, just as in the initial treatment, and then secondarily challenged with 10 μg of OVA plus alum.

Figure 7:
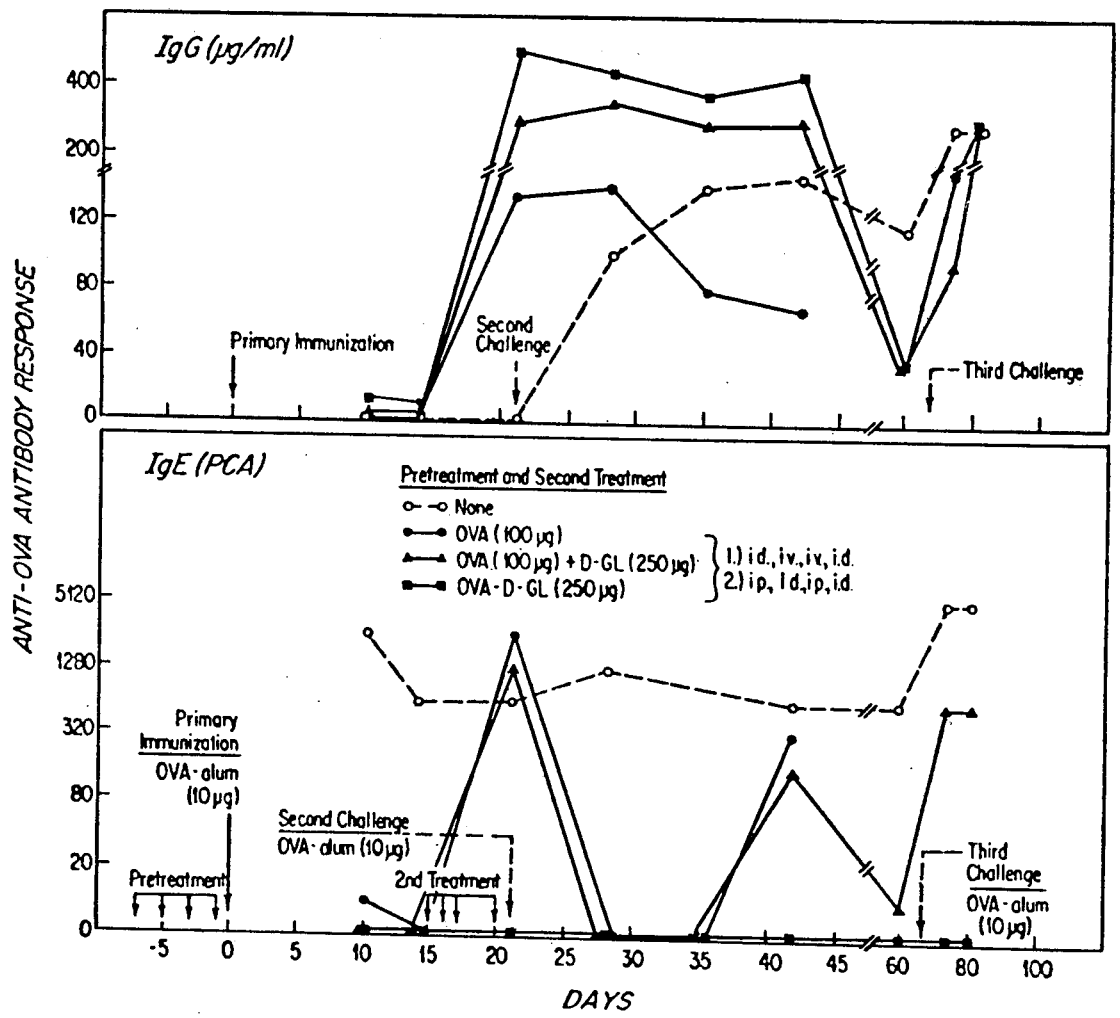
FIG. 7 graphically depicts the OVA-D-GL induction of persistent tolerance in the IgE, but not the IgG, antibody class in CAF$_1$ mice sensitized repeatedly with OVA in alum. Normal CAF$_1$ mice were either not treated or treated with unconjugated OVA (100 $\mu$g) a mixture of unconjugated OVA (100 $\mu$g) plug D-GL (250 $\mu$g) or OVA-D-GL (250 $\mu$g D-GL containing 100 $\mu$g OVA). Pretreated mice were injected 4 times, receiving the dose indicated each time. Doses were administered, by the routes indicated, on alternating days. One day after the 4th dose, all mice were primarily immunized with 10 $\mu$g of OVA in 4 mg of alum. The second treatment was administered on days 15, 16, 17 and 20 and was administered by the routes indicated. A secondary challenge was carried out on day 21 with 10 $\mu$g of OVA in 2 mg of alum. Tertiary challenge was carried out on day 66 in the same manner (all immunizations were given i.p.). Serum IgE (bottom panel) and IgG (top panel) anti-OVA antibody responses of groups of 3 mice bled on various days after primary immunization, as indicated, are illustrated.

As shown in the bottom panel of FIG. 7, control mice developed very good primary and secondary anti-OVA IgE antibody responses. Mice pretreated and later secondarily treated with OVA-D-GL failed to produce detectable anti-OVA IgE antibody responses at any time during the period of observation. This unresponsiveness persisted for a long time, even after a third challenge with the sensitizing dose of OVA administered 45 days after the second treatment with OVA-D-GL. Groups of mice which were treated with either OVA or a mixture of OVA plus D-GL also displayed suppressed IgE antibody responses. The pattern of unresponsiveness in these latter two groups was, however, significantly different from that manifested by mice treated with OVA-D-GL. Thus, in both cases the suppression of IgE antibody production was transient and followed by a rebound production of anti-OVA IgE antibodies at levels that were at times higher than those produced by the untreated control mice. A particularly pertinent contrast in the relative effectiveness of these different modes of treatment is illustrated by the clear ability of mice treated with a mixture of OVA plus D-GL to develop significant IgE anti-OVA responses following tertiary antigenic challenge administered relatively late in the course (day 66), whereas mice treated with OVA-D-GL were totally unresponsive at this time.

In contrast with the clear effectiveness of OVA-D-GL in inducing unresponsiveness in the IgE antibody class, the treatment failed to diminish anti-OVA antibody responses of the IgG class and, moreover, actually appeared to heighten the IgG responses, FIG. 7, top panel). This was true not only of mice treated with either unconjugated OVA or a mixture of D-GL plus OVA. Note that these treated mice produced higher levels of IgG anti-OVA antibodies than the corresponding untreated control mice, particularly during the early stages of observation.

Comparable results were obtained in a separate experiment of similar design using AgE-D-GL as a means for abolishing IgE antibody responses specific for AgE.

Induction of Tolerance in the IgE Antibody Class by Administration of OVA-D-GL to CAF$_1$ Mice Previously Sensitized to OVA Two groups of untreated mice were primarily sensitized with 10 μg of OVA plus alum. Fifteen days later, one group was injected i.d. and i.v. with four doses of OVA-D-GL; the second group was not treated. One day after the last dose of OVA-D-GL, both groups were secondarily challenged with 10 μg of OVA plus alum.

Figure 8:
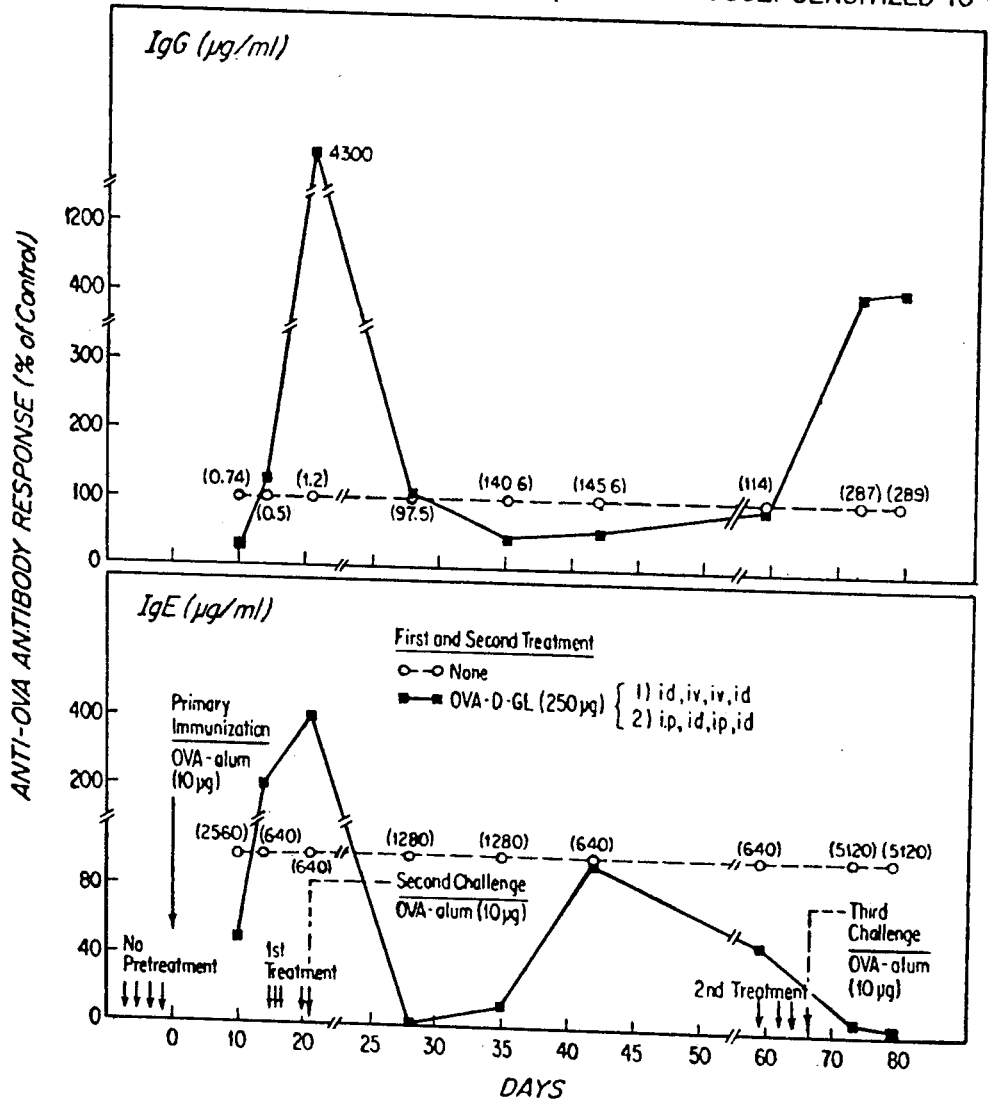
FIG. 8 graphically depicts the induction of tolerance in the IgE antibody class by administration of OVA-D-GL to CAF$_1$ mice previously sensitized to OVA. Normal CAF$_1$ mice were primarily immunized with 10 $\mu$g of OVA in 4 mg of alum on day 0. Two weeks later, one of these groups was treated with OVA-D-GL (250 $\mu$g D-GL containing 10 $\mu$g OVA) administered 4 times, either i.d. or i.v. as indicated, on days 15, 16, 17 and 20 (250 $\mu$g per injection). On day 21, this group and the untreated control mice were secondarily challenged with 10 $\mu$g of OVA in 2 mg of alum. On day 59, the group of OVA-D-GL-treated mice was subjected to a second treatment regimen with OVA-D-GL administered on days 59, 62, 64 and 66 by the routes indicated and in the same dose given for the initial treatment. Also on day 66, both groups were given a tertiary challenge of 10 $\mu$g of OVA in 2 mg of alum. Serum IgE (bottom panel) and IgG (top panel) antibody responses of the treated mice represented as percent of the response developed by the untreated control group with the actual antibody levels of the controls indicated in parenthesis above or below each data point. Each group consisted of 3 mice.

As shown in the bottom panel of FIG. 8, immediately after treatment with OVA-D-GL, and just prior to secondary challenge, such treated mice displayed higher levels of IgE anti-OVA antibodies than the untreated controls. However, in contrast to the untreated group, which developed good secondary responses, the OVA-D-GL-treated mice displayed a sharp drop in their IgE anti-OVA antibody levels. These depressed responses in such treated mice persisted for 15–18 days, follwing which their IgE antibodies rose briefly to normal levels and then subsided to 50% of control titers by day 59. At that time, this group was treated a second time, just as in the initial treatment, and then given a third challenge with 10 μg OVA plus alum. Unlike the untreated control mice which developed substantial tertiary responses following such challenge, the OVA-D-GL treated mice not only failed to respond but, to the contrary, actually displayed diminution of their IgE anti-OVA antibodies to undetectable levels.

The selective nature of tolerance induction for antibodies of the IgE class was again observed in this experiment. As shown in the top panel of FIG. 8, the anti-OVA IgG antibody response of the treated group was 43-fold higher than that exhibited by the untreated controls after the first treatment with OVA-D-GL. This marked hyperresponsiveness in the IgG class subsided such that the OVA-D-GL-treated mice produced comparable levels of IgG antibodies to those of the control group following secondary challenge. However, after the second treatment with OVA-D-GL (day 59), IgG antibody production was again enhanced in the treated mice.

Antigen E-D-GL Induces in the IgE antibody Class When Administered to CAF$_1$ Mice One Year After Initial Sensitization With Antigen E Although the preceding experiments demonstrate the efficacy of protein-D-GL conjugates in inducing specific immunological tolerance in either unsensitized or previously sensitized mice when analyzed in acute circumstance, I wished to ascertain how effective this approach would be in circumstances that more closely approximated a clinical allergy problem. The rationale was, therefore, to sensitize mice, in this case with antigen E, and then let them rest for a period of one year before subjecting them to any further manipulation. Following this prolonged interval, certain mice would be treated, others not, and determinations made of their relative capacities to develop specific antibody responses following subsequent challenge with AgE. The results of such a study are summarized in FIG. 9.

CAF$_1$ mice were exposed to a low dose of whole body ionizing X-irradiation (250 R) shortly prior to primary sensitization with 10 μg of RAG plus alum. The reason for exposing such mice to low doses of X-irradiation pertains to previous investigations in this laboratory that demonstrated that such manipulations resulted in substantial enhancement of the magnitude of IgE antibody production following sensitization with any number of antigens. As shown in the left panel of FIG. 9, this immunization regimen resulted in very good primary IgE anti-AgE antibody responses. Following a one year interval of rest, all of these mice were bled to determine the magnitude of specific anti-AgE IgE antibodies detectable in their serum at that time. It is of interest to note that all mice so tested had detectable IgE antibodies, even though they had not been subsequently exposed to AgE during the one-year rest period.

Mice producing the lowest titers of IgE antibodies (PCA titer-40) were then divided into 3 groups. Two groups were injected i.d. and i.p. with 4 doses of either (1) AgE-D-GL containing 250 μg of D-GL (75 μg of conjugated AgE), or (2) 75 μg of unconjugated AgE. A third group was left untreated as controls. Five days after the last dose, all mice were secondarily challenged with 5 μg of AgE plus alum. As shown in the right panel of FIG. 3, untreated control mice developed excellent secondary IgE antibody responses which peaked 7 days after secondary challenge. Mice treated with unconjugated AgE, although manifesting 50% lower responses than untreated controls on day 7, produced IgE anti-AgE responses either comparable to or 2-fold higher than those controls later in the response. In marked contrast, those mice treated with AgE-D-GL displayed a marked inability to develop anything other than very meager AgE-specific IgE responses.

These results demonstrate the successful induction of specific immunological tolerance (1) to two different protein antigens, OVA and AgE, (2) in both unsensitized and previously sensitized experimental animals, and (3) which is selectively confined to responses of the IgE antibody class. Such tolerance resulted from the administration of appropriate doses of the respective protein-D-GL conjugates. Studies currently underway have documented the absolute antigen specificity of the tolerant state induced with one or the other of the two protein-D-GL conjugates employed here and, moreover, that the mechanism of unresponsiveness obtained with protein-D-GL connugates does not involve the participation of detectable active suppressor cells.

From these data it will be apparent that IgE antibody responses could be suppressed not only by administration of protein-D-GL conjugates, but also by administering comparable doses of unconjugated protein alone. It should be emphasized, however, that the patterns of IgE antibody production following treatment in each of these two ways were significantly different. Thus, in general, administration of unconjugated protein suppressed IgE production effectively, but only transiently; in one case of particular note, namely when treatment was administered after a one year interval of rest following initial sensitization, administration of unconjugated protein had only marginal inhibitory effects on the specific response, and this effect was shortly followed by a marked "booster" effect on the specific IgE response. Admininstration of protein-D-GL conjugates, on the other hand, resulted in inhibition of IgE antibody production which persisted for long periods of time, even after repeated exposure to the sensitizing antigen. I have no information at the present time with regard to whether the mechanism of tolerance induced by these two different methods is qualitatively the same or different, but experiments in progress are designed to address this important question.

A second point worth emphasizing is the remarkable selectivity of unresponsiveness observed in these studies. IgE antibody responses were markedly diminished while, concomitantly, specific IgG antibody responses to the same determinants tended to be increased, irrespective of whether protein-D-GL conjugates or unconjugated proteins were administered to test mice. This represents a major difference between the protein-D-GL system and the hapten-D-GL systems studied earlier; in the latter systems, it was clear that antibody responses of all immunoglobulin classes were susceptible to tolerance induction following exposure to hapten-D-GL conjugates. I have no data at present that would help to explain the selectivity of protein-D-GL conjugates for responses of the IgE class, and further studies are necessary to clarify this point. Possibly, the relative concentration of protein determinants on a given D-GL molecule may determine the extend of Ig class selectivity observed. Nevertheless, it is clear that fundmental differences exist in the susceptibility to tolerance induction of the IgE and IgG antibody systems, respectively, under the conditions of the experiments reported here. Establishment of the basis for this difference will be of great significance in furthering our understanding of regulatory control of these two antibody classes.

In the hapten-D-GL tolerance models, substantial evidence has been previously obtained demonstrating the rapid and irreversible inactivation of B lymphocytes specific for the hapten-employed after brief exposure to the conjugate, possibly by disturbance of normal membrane machinery. The mechanism of tolerance induction by protein-D-GL conjugates has yet to be established. The conjugate may be acting directly on B lymphocytes, notably those of the IgE class, on protein-specific T lymphocytes (of either helper or suppressor type, or both) or on both B and T lymphocytes. Studies in other laboratories have recently demonstrated that antigen-specific suppressor T cells, capable of suppressing IgE antibody production, can be generated in experimental animals by administering urea-denatured antigen or protein coupled to polyethylene glycol. In the latter study, controls for the suppressive effects of unconjugates protein were not reported, thus leaving open the possibility that the suppression obtained with protein-polyethylene glycol conjugates may be similar to that obtained with unconjugated protein alone, as demonstrated in the present study. While inhibition of IgE antibody production by the function of antigen-specific T cells is itself important, the practicality of such approaches as a therapeutic modality are not expected to be far-reaching due to the transient nature of such suppression phenomena.

It should be noted that one recent report claimed that DNP-D-GL induced DNP-specific suppressor T cells in a murine system. However, since the experimental conditions employed were not adequate for eliminating the possible carry-over of tolerogenic DNP-D-GL molecules in the cell mixtures, this interpretation may not be valid. Nevertheless, as state above, there is no a priori reason not to consider that the mechanisms of tolerance induction with hapten-D-GL and protein-D-GL conjugates, respectively, could be quite different.

The obvious implication of our results is that allergenic proteins coupled with D-GL may prove useful in man for the specific abrogation of IgE antibody responses to the relevant allegen in those IgE-mediated disorders where the nature of the predominant sensitizing proteins are known. The fact that protein-D-GL conjugates induce selective inhibition of IgE antibody production, while not diminishing IgG antibody responses against the same antigen, meets criteria for ideal properties of therapeutic agents of this type to use in human allegic diseases.

Conjugation, purification and quantitation procedures such as those described here and the concept of application of the avidin-biotin system are regarded as widely applicable to preparation of conjugates of proteins, protein-polypeptides and protein-polysaccharides for a variety of experimental purposes in which such substances may be of value.

REFERENCES*

Bayer, E. and Wilchek, M. (1974) *Methods Enzymol.* 34, 265.

Bayly, R. J. and Evans, E. A. (1966) *J. Labelled Compd.* 2, 1.

Chiorazzi, N., Eshhar, Z., and Katz, D. H. (1976) *Proc. Natl. Acad. Sci. USA* 73, 2091.

Cunningham, L. W. and Nuenke, B. J. (1961) *J. Biol. Chem.* 236, 1716.

David, G. W. (1972) *Biochem. Biophys. Res. Commun.* 48, 464.

David, G. S. and Reisfeld, R. A. (1974) *Biochemistry.* 13, 1014.

Ellman, G. L. (1959) *Arch. Biochem. Biophys.* 82, 70.

Eshhar, Z., Benacerraf, B. and Katz, D. H. (1975) *J. Immunol.* 114, 872.

Gennis, R. B. and Cantor, C. R. (1972) *Biochemistry.* 11, 2509.

Glover, J. S., Salter, D. N. and Sheperd, B. P. (1967) *Biochem. J.* 103, 120.

Green, N. M. (1970) *Methods Enzymol.* 18A, 418.

Green, N. M. and Toms, E. J. (1973) *Biochem. J.* 133, 687.

Green, N. M. (1975) *Adv. Prot. Chem.* 29, 84.

Greenwood, F. C., Hunter, W. M. and Glover, J. S. (1963) *Biochem. J.* 89, 114.

Jasiewicz, M. L., Schoenberg, D. R. and Mueller, G. C. (1976) *Exp. Cell Res.* 100, 213.

Kato, K., Hamaguchi, Y., Fukui, H., and Ishikawa, E. (1975) *J. Biochem.* 78, 235.

Kato, K., Hamaguchi, Y., Fukui, H., and Ishikawa, E. (1976) *Eur. J. Biochem.* 62, 285.

Katz, D. H. (1974) In *Immunological Tolerance: Mechanisms and Potential Therapeutic Applications.* (Katz, D. H. and Benacerraf, B., eds.), Academic Press, New York.

Kitagawa, T. and Aikawa, T. (1976) *J. Biochem.* 79, 233.

Klotz, I. M. and Heiney, R. E. (1962) *Arch. Biochem. Biophys.* 96, 605.

Lindsay, D. G. and Shall, S. (1971) *Biochem. J.* 121, 737.

Liu, F. -T., and Leonard, N. J. (1978) *J. Amer. Chem. Soc.* 100, 0000 (1978).

Liu, F. -T., Zinnecker, M., Hamoaka, T., and Katz, D. H. (1978) *Fed. Proc.* 37, 1375.

Lowry, O. H., Rosenbrough, N. J., Farr, A. L., and Randall, R. J. (1951) *J. Biol. Chem.* 193, 265.

Maloy, W. L. (1977) *Fed. Proc.* 36, 873.

Smyth, D. G., Nagamatsu, A., and Fruton, J. S. (1960) *J. Amer. Chem. Soc.* 82, 4600.

Katz, D. H., Davie, J. M., Paul, W. E. and Benacerraf, B. (1971) *J. Exp. Med.* 134, 201-223.

Katz, D. H., Hamaoka, T. and Benacerraf, B. (1972) *J. Exp. Med.* 136, 1404-1429.

Davie, J. M., Paul, W. E., Katz, D. H. and Benacerraf, B. (1972) *J. Exp. Med.* 136, 426-438.

Nossal, G. J. V., Pike, B. L. and Katz, D. H. (1973) *J. Exp. Med.* 138, 312-317.

Hamaoka, T. and Katz, D. H. (1974) *J. Exp. Med.* 139, 1446-1463.

Ault, K., Unanue, E. R., Katz, D. H. and Benacerraf, B. (1974) *Proc. Nat. Acad. Sci. U.S.A.* 71, 3111-3114.

Katz, D. H., Hamaoka, T. and Benacerraf, B. (1973) *Proc. Nat. Acad. Sci. U.S.A.* 70, 2776-2780.

Katz, D. H., Stechschulte, D. H. and Benacerraf, B. (1975) *J. Allergy Clin. Immunol.* 55, 403-410.

Liu, F. T., Zinnecker, M., Hamaoka, T. and Katz, D. H. (1979) *Biochemistry* 18, 000-

Chiorazzi, N., Tung, A. S. and Katz, D. H. (1977) *J. Exp. Med.* 146, 302-308.

Katz, D. H., Hamaoka, T., Newburger, P. E. and Benacerraf, B. (1974) *J. Immunol.* 113, 974-984.

Pierce, S. K. and Klinman, N. R. (1975) *J. Exp. Med.* 142, 1165-1176.

Chiorazzi, N., Fox, D. A. and Katz, D. H. (1976) *J. Immunol.* 117, 1629-1639.

Chiorazzi, N., Fox, D. A. and Katz, D. H. (1977) *J. Immunol.* 118, 48-57.

Takatsu, K., Ishizaka, K. and King, T. P. (1975) *J. Immunol.* 115, 1469-1476.

Lee, W. Y. and Sehon, A. H. (1978) *Int. Archs Allergy Appl. Immun.* 56, 193-206.

Kim, Y. T., Mazer, T., Weksler, M. E. and Siskind, G. W. (1978) *J. Immunol.* 121, 1315.

*The above-listed references are incorporated herein as though fully set forth. Additional background information may be found in the publications cited in the above references.

I claim as my invention:

1. The method of preparing therapeutic immunosuppressive conjugates of D-glutamic acid-D-lysine copolymer with antigen comprising the steps of:
    (a) introducing biotin into the D-glutamic acid-D-lysine copolymer molecule to form D-GL(biotin);
    (b) reacting D-GL(biotin) with either m-maleimidobenzoyl-N-hydroxysuccinimide ester to form MB-D-GL(biotin) or with S-acetylmercaptosuccinic anhydride to form SH-D-GL(biotin);
    (c) reacting antigen with either m-maleimidobenzoyl-N-hydroxysuccinimide ester to form MB-Antigen or with S-acetylmercaptosuccinic anhydride to form SH-Antigen;
    (d) reacting MB-D-GL(biotin) with SH-Antigen or reacting SH-D-GL(biotin) with MB-Antigen to form conjugates of D-glutamic acid-D-lysine(biotin) with antigen; and
    (e) separating said D-glutamic acid-D-lysine(biotin)-antigen conjugate from non-conjugated antigen by affinity chromatography on an avidin-Sepharose chromatographic column.

2. The method of preparing therapeutic immunosuppressive conjugates of D-glutamic acid-D-lysine copolymer with insulin comprising the steps of:
    (a) introducing biotin into the D-glutamic acid-D-lysine copolymer molecule to form D-GL(biotin);
    (b) reacting D-GL(biotin) with either m-maleimidobenzoyl-N-hydroxysuccinimide ester to form MB-D-GL(biotin) or with S-acetylmercaptosuccinic anhydride to form SH-D-GL(biotin);
    (c) recting insulin with either m-maleimidobenzoyl-N-hydroxysuccinimide ester to form MB-Insulin or with S-acetylmercaptosuccinic anhydride to form SH-Insulin;
    (d) reacting MB-D-GL(biotin) with SH-Insulin or reacting SH-D-GL(biotin) with MB-Insulin to form conjugates of D-glutamic acid-D-lysine(biotin) with insulin; and
    (e) separating said D-glutamic acid-D-lysine(biotin)-insulin conjugate from non-conjugated insulin by affinity chromatography on an avidin-Sepharose chromatographic column.

3. The method of preparing therapeutic immunosuppressive conjugates of D-glutamic acid-D-lysine copolymer with ragweed antigen E comprising the steps of:
    (a) introducing biotin into the D-glutamic acid-D-lysine copolymer molecule to form D-GL(biotin);
    (b) reacting D-GL(biotin) with either m-maleimidobenzoyl-N-hydroxysuccinimide ester to form MB-D-GL(biotin) or with S-acetylmercaptosuccinic anhydride to form SH-D-GL(biotin);
    (c) reacting ragweed antigen E with either m-maleimidobenzoyl-N-hydroxysuccinimide ester to form MB-ragweed antigen E or with S-acetylmercaptosuccinic anhydride to form SH-ragweed antigen E;
    (d) reacting MB-D-GL(biotin) with SH-ragweed antigen E or reacting SH-D-GL(biotin) with MB-ragweed antigen E to form conjugates of D-glutamic acid-D-lysine(biotin) with ragweed antigen E; and
    (e) separating said D-glutamic acid-D-lysine(biotin)-ragweed antigen E conjugate from non-conjugated ragweed antigen E by affinity chromatography on an avidin-Sepharose chromatographic column.

* * * * *

UNITED STATES PATENT AND TRADEMARK OFFICE
CERTIFICATE OF CORRECTION

PATENT NO. : 4,276,206
DATED : June 30, 1981
INVENTOR(S) : David H. Katz

It is certified that error appears in the above-indentified patent and that said Letters Patent is hereby corrected as shown below:

Column 1, line 4, insert the following:
This invention was made with government support under Grant Number AI 13874 and AI 13781 awarded by the National Institute of Health. The government has certain rights in the invention.

Signed and Sealed this

Twelfth Day of April, 1994

Attest:

BRUCE LEHMAN

Attesting Officer

Commissioner of Patents and Trademarks